United States Patent [19]

Goodwin

[11] Patent Number: 5,846,807
[45] Date of Patent: Dec. 8, 1998

[54] MEDIA COMPOSITIONS FOR THREE-DIMENSIONAL MAMMALIAN TISSUE GROWTH UNDER MICROGRAVITY CULTURE CONDITIONS

[75] Inventor: Thomas J. Goodwin, Friendswood, Tex.

[73] Assignee: The United States of America as represented by the Administrator of the National Aeronautics and Space Administration, Washington, D.C.

[21] Appl. No.: 600,793

[22] Filed: Feb. 13, 1996

Related U.S. Application Data

[60] Division of Ser. No. 66,292, May 25, 1993, Pat. No. 5,496,722, which is a continuation-in-part of Ser. No. 939,791, Sep. 3, 1992, Pat. No. 5,308,764, which is a continuation of Ser. No. 317,391, Mar. 2, 1989, Pat. No. 5,153,132, which is a continuation-in-part of Ser. No. 317,776, Mar. 2, 1989, Pat. No. 5,155,034, which is a continuation-in-part of Ser. No. 213,588, Jun. 30, 1988, Pat. No. 5,235,161, which is a continuation-in-part of Ser. No. 213,559, Jun. 30, 1988, Pat. No. 4,988,623, which is a continuation-in-part of Ser. No. 625,345, Dec. 11, 1990, Pat. No. 5,153,131.

[51] Int. Cl.$^6$ ..................................................... C12N 5/00
[52] U.S. Cl. ................................... 435/240.3; 435/240.31
[58] Field of Search .......................... 435/240.23, 240.3, 435/240.31

[56] References Cited

U.S. PATENT DOCUMENTS

| | | | |
|---|---|---|---|
| 3,883,393 | 5/1975 | Knazek et al. | 195/1.8 |
| 4,220,725 | 9/1980 | Knazek et al. | 435/285 |
| 4,352,887 | 10/1982 | Reid et al. | 435/240 |
| 4,757,017 | 7/1988 | Cheung | 435/240.23 |
| 4,940,853 | 7/1990 | Vandenburgh | 435/240.23 |
| 4,963,489 | 10/1990 | Naughton et al. | 435/240.1 |
| 4,988,623 | 1/1991 | Schwarz et al. | 435/286 |
| 5,026,637 | 6/1991 | Soule et al. | 435/29 |
| 5,026,650 | 6/1991 | Schwarz et al. | 435/286 |
| 5,032,508 | 7/1991 | Naughton et al. | 435/32 |
| 5,153,131 | 10/1992 | Wolf et al. | 435/240.24 |
| 5,153,132 | 10/1992 | Goodwin et al. | 435/240.24 |
| 5,155,034 | 10/1992 | Wolf et al. | 435/240.24 |
| 5,155,035 | 10/1992 | Schwarz et al | 435/240.24 |
| 5,308,764 | 5/1994 | Goodwin et al. | 435/240.24 |

OTHER PUBLICATIONS

"Cell and Environment Interactions in Tumor Microregions: The Multicell Spheroid Model", Robert M. Sutherland, Science, vol. 240, pp. 177–184, 8 Apr. 1988.

"Defining Conditions to Promote the Attachment of Adult Human Colonic Epithelial Cells", Buset et al, In Vitro Cellular & Development Biology, vol. 23, #6, pp. 403–412, Jun. 1987.

"Culturiing Hepatocytes and Other Differentiated Cells", Lola M. Reid et al, Hepatology, vol. 4, #3,, pp. 548–558, 1984.

"Retention of Differentiated Characteristics in Human Fetal Keratinocytes in Vitro", Haake et al, In Vitro Cell. & Dev. Biol., vol. #25, pp. 592–600, Jul. 1989.

"Clonal Growth of Human Prostatic Epithelial Cells is Stimulated by Fibroblasts", John N. Kabalin et al, The Prostate vol. 14, pp. 251–263, 1989.

"The Colonic Pericryptal Fibroblast Sheath: Replication, Migration, and Cytodifferentiation of a Mesenchymal Cell System in Adult Tissue". Gordon I. Kave et al. Gastroenterology, vol. 60, #4, pp. 515–536, 1971.

"Epithelial Polarity, Villin Expression, and Enterocytic Differentiation of Cultured Human Colon Carcinoma Cells: A Survey of Twenty Cell Lines", Isabelle Chantret et al, Cancer Research, vol. 48, pp. 1936–1942, Apr. 1, 1988.

"Stimulation of Intestinal Epithelial Cell Proliferation in Culure by Growth Factors in Human and Ruminant Mammary Secretions", A. N. Corps et al, J. Endocr., vol. 113, pp. 285–290, Nov. 3, 1986.

"Effect of Epidermal Growth Factor on Ontogeny of the Gastrointestinal Tract", E. V. O'Loughlin et al, Am. J. Physiol., vol. 249, pp. G674–G678, Jul. 8, 1985.

"Contradistinctive Growth Responses of Cultured Rat Intestinal Epithelial Cells to Epidermal Growth Factor Depending on Cell Population Density", Johathan Blay et al, Journal of Cellular Physiology, vol. 129, pp. 343–346, Jul. 15, 1986.

"Morphologic Differentiation of Colon Carcinoma Cell Lines HT–29 and HT–29KM in Rotating—Wall Vessels", Thomas J. Goodwin et al, In Vitro Cell. Dev. Biol., vol. 28A, pp. 47–60, Jan. 1992.

"Colon Organ Culture as a Model for Carcinogenesis", Abulkalam M. Shamsuddin, Colon Cancer Cells, Moyer and Poste, Eds. Academic Press, Inc., 1990.

"Methods for Propagation and Characterization of Human GI and Other Cells for Study of HIV", Moyer, J. Tiss. Cult. Meth., vol. 13, pp. 107–116, 1991.

*Primary Examiner*—Blaine Lankford
*Attorney, Agent, or Firm*—James M. Cate

[57] ABSTRACT

Normal mammalian tissue and the culturing process has been developed for the three groups of organ, structural and blood tissue. The cells are grown in vitro under microgravity culture conditions and form three dimensional cells aggregates with normal cell function. The microgravity culture conditions may be microgravity or simulated microgravity created in a horizontal rotating wall culture vessel.

10 Claims, 6 Drawing Sheets

MEDIA COMPOSITIONS FOR THREE-DIMENSIONAL MAMMALIAN TISSUE GROWTH UNDER MICROGRAVITY CULTURE CONDITIONS

This is a divisional of application Ser. No. 08/066,292 filed May 25, 1993, now U.S. Pat. No. 5,496,722, which is a continuation-in-part of application Ser. No. 07/939,791, filed Sep. 3, 1992, now U.S. Pat. No. 5,308,764, which is a continuation of application Ser. No. 07/317,391, filed Mar. 2, 1989, now U.S. Pat. No. 5,153,132, which is a continuation-in-part of application Ser. No. 07/317,776, filed Mar. 2, 1989, now U.S. Pat. No. 5,155,034, which is a continuation-in-part of application Ser. No. 07/213,588, filed Jun. 30, 1988, now U.S. Pat. No. 5,235 161; and this is also a continuation-in-part of application Ser. No. 07/213,559, filed Jun. 30, 1988, now U.S. Pat. No. 4,988,623, and a continuation-in-part of application Ser. No. 07625,345, filed Dec. 11, 1990, now U.S. Pat. No. 5,153,131,

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 42 U.S.C. 2457).

FIELD OF THE INVENTION

The invention relates to production of functional three dimensional mammalian tissue from a culture of normal cells in fluid media.

BACKGROUND OF THE INVENTION

The culturing of mammalian cells presents many challenges as compared to bacteria, yeast and molds. Bacterial-type cells have tougher outer cell walls and can be manipulated without injuring the cells during culture, whereas mammalian cells are delicate and cannot withstand stress. Bacterial-type cells are not organized into functional tissue groups with cell differentiation or organization as seen in higher life forms such as mammals.

Mammalian tissue can be grouped into three general categories of (1) organ tissue (2) structural tissue and (3) blood producing tissue. Mammalian tissue is composed of aggregates of cells that share a functional interrelationship in order to have tissue growth. Mammalian tissue is composed of different types of cells characterized by different morphology and immunochemical properties. Cellular differentiation in mammals involves complex interactions in which cell membrane junctions, extracellular matrices such as basement membrane and ground substances. Soluble signals produced and shared among the cells play an important role.

Study of normal mammalian tissue, however, has been limited because of lack of adequate in vitro culture systems that product tissue of sufficient size and functionality. In contrast, tumor cells are by their nature easier to grow in vitro, possess abnormal growth characteristics and do not behave like normal cells in their interaction with neighboring cells. Sutherland, "Cell and Environment Interactions in Tumor Microregions: The Multicell Spheroid Model", *Science*, Vol. 240, pp. 177–240, 8 Apr. 1988. Different culture methods for normal and abnormal mammalian cells have been used. Elaborate culture systems for normal mammalian cells have been developed in an attempt to grow normal tissue.

A variety of different cells and tissues, such as bone marrow, skin, liver, pancreas, mucosal epithelium, adenocarcinoma and melanoma, have been grown in culture systems to provide three dimensional growth in the presence of a preestablished stromal support matrix. U.S. Pat. No. 4,963,489, Three-Dimensional Cell and Tissue Culture System, Naughton, et al., Oct. 16, 1990; U.S. Pat. No. 5,032,508, Three-Dimensional Cell and Tissue Culture System, Naughton, et al., Jul. 16, 1991. A biocompatible, non-living material formed into a three dimensional structure is inoculated with stromal cells. In some cases, the three dimensional structure is a mesh pre-coated with collagen. Stromal cells and the associated connective tissue proteins naturally secreted by the stromal cells attach to and envelop the three dimensional structure. The interstitial spaces of the structure become bridged by the stromal cells, which are grown to at least subconfluence prior to inoculating the three dimensional stromal matrix with tissue-specific cells.

Normal mammalian tissue has been grown for limited periods of time as two-dimensional monolayers on gelled substrate or other surface for anchoring the cells. Adult colonic epithelial cells have been found to be more difficult to culture than fetal colonic epithelial cells. Buset et al. "Defining Conditions to Promote the Attachment of Adult Human Colonic Epithelial Cells", *In Vitro Cell. & Dev. Biol.*, Vol. 23. No. 6 pp. 403–412 (June 1987). To mimic a more normal environment using monolayer culture, cocultures were prepared using two cell types, often with a "feeder layer" of fibroblasts or other cells to supply the primary cells with nutrients and other factors difficult to incorporate into a substrate and to provide the cellular interaction believed to be necessary for the production of differentiated tissue. Reid et al., "Culturing Hepatocytes and Other Differentiated Cells", *Hepatology*, Vol. 4, No. 3, pp. 548–559 (1984); Haake et al. "Retention of Differentiated Characteristics in Human Fetal Keratinocytes In Vitro", *In Vitro Cell. & Dev. Biol.*, Vol. 25 No. 25 pp. 592–600 (July 1989). Also, monolayers "conditioned" with fibroblast cells have been used to impart into the substrate the soluble growth factors for epithelial cells. Kabalin et al. "Clonal Growth of Human Prostatic Epithelial Cells Is Stimulated by Fibroblasts", *The Prostate*, Vol. 14, pp. 251–263 (1989). Monolayers do not produce a three dimensional tissue, but rather a two-dimensional spread of cells. Often the cells developed by monolayer culture and coculture become undifferentiated and lack normal function.

Three dimensional in vitro models of differentiated tissue have been produced, however, the cells often do not demonstrate normal cellular activity. Embryonic avian skeletal muscle cells have been grown in vitro on expandable membranes which are gradually and substantially, continuously stretched to simulate the mechanical stimulation of cells experienced in vivo. U.S. Pat. No. 4,940,853, Method for Growing Tissue Specimens in Vitro, Vadenburgh, Jul. 10, 1990. The expandable support membrane supports development of three dimensional structures which more closely resemble tissue grown in vivo, however, normal independent cellular activity was not identified. Additionally, three dimensional human mammary epithelial cells have been grown in collagen. U.S. Pat. No. 5,026,637, Soule, et al., Jun. 25, 1991. However, the cells, under the culture conditions, did not undergo terminal differentiation and cell senescence, but rather were "immortal" in that they retained the capacity to divide forever. Thus, normal cellular activity and naturalization was not observed.

The study of the organ systems exemplifies the complex interrelationship of neighboring cells in mammalian tissue necessary for normal three dimensional tissue growth. Mammalian organ systems have been studied to determine the relationship of the cell types that make up the organ as well as their effects on each other. Studies on normal tissue differentiation have indicated an important interaction between epithelial cells and mesenchymal cells and the production and differentiation of the cells from fibroblasts. Kaye et al., "The Colonic Pericryptal Fibroblast Sheath: Replication, Migration, and Cytodifferentiation of a Mesenchymal Cell System in Adult Tissue" *Gastroenterology*, Vol. 60. No. 4, pp. 515–536 (1971). Furthermore, small intestine tissue is exemplary of organ tissue types with epithelial cells with functional brush borders and organized columnar cells associated with mesenchymal cells. Other organs have similar organization. Small intestine tissue has physical support in vivo so that the tissue forms crypts which increase the surface area of the organ. In addition to the crypt formation in vivo, there are also immunocytochemical markers for particular cell types with normal functionality as well as cell types that are in developmental phases to produce functional organ tissue.

Immunochemical properties further characterize normal cells types and tissue. Keratin, vimentin and Factor VIII antibodies detect epithelial, fibroblastic and endothelial cells respectively. Villin is a cytoskeletal protein only found in epithelial cells from the small intestine and colon. The angioblast marker is present in certain precursor endothelial cells, particularly dividing cells. Sucrase is an enzyme found in the epithelial cell brush border of the small intestine. Basement membrane and extracellular matrix components such as laminin, fibronectin, Collagen IV, and proteoglycan are associated with ordering of tissue and cellular polarity. Basement membrane and extracellular matrix development has been related to epithelial-mesenchymal development and differentiation. All these components are necessary for normal tissue growth.

Culture of normal or neoplastic small intestine epithelium as large-scale three dimensional configurations has not been shown with routinely used in vitro culture technology. Chantret et al., "Epithelial Polarity, Villin Expression and Eterocytic Differentiation of Cultured Human Colon Carcinoma Cells: A survey of Twenty Cell Lines" *Cancer Res.*, Vol. 48, pp. 1936–1942 (Apr. 1, 1988). Factors that control proliferation and differentiation in the gastrointestinal tract remain largely unknown. Corps et al., "Stimulation of Intestinal Epithelial Cell Proliferation in Culture by Growth Factors in Human and Ruminant Mammary Secretions" *J. Endocr.*, Vol. 113, pp. 285–290 (3 Nov. 1986); O'Loughlin et al., "Effect of Epidermal Growth Factor on Ontogeny of the Gastrointestinal Tract" *Am. J. Physiol.*, Vol. 249, pp. G674–G678 (8 Jul. 1985); Blay et al., "Contradistinctive Growth Responses of Cultured Rat Intestinal Epithelial Cells to Epidermal Growth Factor Depending on Cell Population Density" *J. of Cell. Physiol.*, Vol. 129, pp.343–346 (15 Jul. 1986).

Cartilage tissue is exemplary of normals structural tissue. Attempts have been made to encourage cartilage formation in vitro by culturing chondrocytes. Typical culture durations achieved in the more successful instances range from 10 days to 30 days, the 30-day point being a transition towards static culture or cellular degeneration and death. The success achieved to date has had limited 3-dimensionality. Typical cell culture methodologies include isolating chondrocytes from various articular surfaces and plating the isolated chondrocytes as a monolayer in a T-flask. Various manipulations were then utilized to encourage chondrocyte expansion and differentiation, and the deposition of proteoglycan into the interstitial matrices. These maneuvers include various growth factor augmentations, an effort to emulate in situ conditions. The extent to which the cells can be maintained in situ is on the order of tens of years as seen in the normal adult. Conversely, in standard cell culture the extent which cells can be maintained in a growth phase or a normal static maintenance phase is on the order of 22 days. It has been demonstrated that multiple cell-surface receptors exist that are important in cellular growth and differentiation, and extracellular matrix formation. Cell surface receptors are labile to destructive cell surface sheer.

Cartilage cells were reportedly cultured for 13 months using a solid substrate in conventional culture vessels. U.S. Pat. No. 4,757,017 Cheung et al., Jul. 12, 1988. The solid substrate was a porous calcium compound. Multilayer cell growth was observed and the cells maintained their phenotype.

Bone marrow has been grown using conventional monolayer cell culture technique. Human bone marrow cell culture technique. Human bone marrow cell production declines over time in monolayer culture. Naughton et. al. disclosed a bone marrow culture system in co-culture with stromal cells or mixtures of cell types on a three dimensional support. U.S. Pat. No. 4,963,489. The three dimensional support was coated by cells such as fetal fibroblasts over a collagen layer on a mesh support.

Mammalian tissue has been grown in bioreactors providing low shear from abnormal cell types such as tumor cells or cocultures with normal and tumor cells. Goodwin et al., "Morphological Differentiation of Colon Carcinoma Cell Lines HT-29 and HT-29K in Rotating-Wall Vessels," *In Vitro Cell. Dev. Biol.* Vol. 28A, pp. 47–60, January 1992. The bioreactor designs are disclosed in U.S. Pat. Nos. 4,988,623; 5,026,650 and 5,153,131. Co-culture of tumor and normal cells in solid-state culture has been reported as shown in U.S. Pat. No. 4,352,887 to Reid et al. issued Oct. 5, 1982. However, since tumor or abnormal cells grow under conditions that normal cells cannot tolerate, the growth of non-normal cells does not predict success for normal mammalian culture under the same or similar culture conditions.

There are many potential uses of artificially produced tissue for different mammalian systems. For example, small intestine tissue can be used as a model for the molecular and clinical treatment of diseases such as inflammatory bowel disease (Crohn's, ulcerative colitus), malabsorptive syndromes (short-gut syndrome), numerous infectious diseases and tumors of the small bowel. The tissue can be a model for the therapeutic trials prior to in vivo experimentation. However cultures longer than 7 weeks have been difficult to achieve, since crypt cells are unable to survive standard culture regimens, and two-dimensional organ cultures do not support the de novo assembly of stroma and its contribution to epithelial cell growth. Shamsuddin, "Colon Organ Culture as a Model for Carcinogenesis", *Colon Cancer Cells*, Moyer and Poste, Eds. Academic Press, Inc. 1990.

Also, a mammalian structural tissue such as a cartilage model of high fidelity is important in clinical studies. There are numerous maladies associated with cartilage, including but not limited to knee-joint injuries, back injuries, articular-surface injuries, inflammatory diseases such as arthritis and temporal-mandibular joint disease. Beyond the diseases are the natural processes of maturation through puberty and the geriatric inability to repair and maintain articular surfaces. A tissue model would be beneficial for the analyses and development of therapeutic protocols. Moreover, these models become essential in tailoring pharmaceuticals, i.e.; nonsteroidal anti-inflammatories where the pharmaceutical may actually become detrimental to the chondrocyte by way of degradation into secondary metabolites.

The artificial production of functional blood tissue such as normal bone marrow could be used in patients in need of bone marrow replacement which have lost the ability to produce the tissue. The tissue could be grown from a sample and transplanted back to the patient. Also, bone marrow material can be transplanted into a non-autologous recipient.

SUMMARY OF THE INVENTION

Aggregates of normal mammalian cells have been produced in vitro for each of the three major tissue groups. The cell aggregates exhibited three dimensional tissue growth and functional interrelationship by cell to cell contact. Functional cells with normal morphology have been produced for organ, structural and blood producing tissues. Cell function was in some cases confirmed immunohistochemically by antibodies specific to particular cellular components characterizing cell types.

The aggregates were produced under "microgravity culture conditions" which can be microgravity or simulated microgravity. Simulated microgravity was created in unit gravity by controlling the horizontal rotation of a culture vessel containing normal mammalian cells, culture matrix and completely filled with culture media. In the preferred process a horizontally rotating wall culture vessel produced the simultaneous conditions of (1) collocation of cells and culture matrix with similar or differing sedimentation properties in a similar spatial region, (2) freedom for three dimensional spatial orientation of tissues formed by the culturing of the cells and (3) low shear and essentially no relative motion of the culture environment with respect to the walls of the culture vessel. The culture conditions included mass transfer under microgravity conditions with exchange of nutrients for metabolic waste and appropriate gas exchange in the culture system.

The process for producing the normal mammalian tissue is particularly unique in that the resultant product is normal tissue of a size of 2 millimeters and larger. The size of the tissue cultured is significant because assembly of three dimensional masses of this size is not possible without the complex functional interrelationship of the normal mammalian cells.

Functional three dimensional organ tissue masses have been produced artificially from an inoculum of predominantly normal differentiated epithelial cells and predominantly normal differentiated mesenchymal cells. The epithelial and mesenchymal cells were preferably disassociated prior to introduction into the culture vessel. The epithelial and mesenchymal cells were introduced in a vessel with a culture matrix preferably of generally spherical microcarriers. Tissue engineering was achieved by selected introduction of the mesenchymal cells and culture matrix for a preselected culture period prior to transfer of epithelial cells to the culture vessel.

A three dimensional normal organ tissue mass grew in association with the culture matrix having functional epithelial cells and functional mesenchymal cells. Also, the tissue developed cells immunochemically characterized as functional endothelial precursor cells in significantly greater numbers than were present in the initial inoculum. The organ tissue mass also developed cells immunochemically characterized as functional angioblasts and cells that were immunochemically characterized as functional epithelial cell brush borders. Organized columnar cells were clearly visible. The developing organ tissue included cells immunochemically characterized as basement membrane components. As the tissue masses grew anchored to microcarriers they were joined with cord-like structures of fibroblasts covered by epithelial cells.

A preferred fluid media for mammalian organ tissue culture is a MEM (minimum essential medium) base with a tri-sugar supplement and fetal bovine serum. The preferred tri-sugar supplement is selected from mixtures of fructose, galactose and glucose.

The organ tissue can be initiated by various normal mammalian organ cells including skin, small intestine, pancreas, liver, colon, and endocrine gland. Predominantly normal terminally differentiated cells were able to revert to a state that allowed interaction of a growing cellular mass capable of normal organ tissue evolution without using non-differentiated cells and without using cell types such as tumor cells that have abnormal cell growth characteristics.

Artificially produced structural tissue has been produced in microgravity culture conditions from normal structural tissue. The three dimensional structural tissue mass developed with functional chondrocytes and stromal cells with tissue calcification. The tissue exhibited matrix deposition including cells immunochemically characterized as producing Type IV, Type IX and Type X collagen. The structural tissue is cultured in a vessel at microgravity conditions as described herein with a culture matrix. A preferred culture matrix was generally spherical microcarriers. An initial inoculum used in the process to produce the structural tissue mass was nonhuman embryonic cartilage cells disassociated prior to transfer to the culture vessel.

Three dimensional mammalian blood tissue of normal origin has been produced artificially. The bone marrow tissue was prepared from normal bone marrow cells. The inoculum from the bone marrow include pleuripotential stem cells, fully matured white blood cells and red blood cells. The bone marrow cells were transferred into a culture vessel with fluid culture media and culture matrix. Microgravity culture conditions as described herein were maintained while three dimensional tissue growth was achieved. The culture matrix can be disc-shaped. The bone marrow can be encased in stromal-like matrices and introduced into the vessel. Also, culture matrix of Type I rat tail collagen and biopolymers can be used.

Relatively large normal mammalian three dimensional tissue masses were cultured using microgravity culture conditions. The ability of the cells to grow into large aggregates supports the functional relationship achieved by cell to cell contact of normal cells. The process and normal tissue of this invention can be used advantageously as an in vitro produced mammalian product.

DETAILED DESCRIPTION OF THE INVENTION

Figure 1:
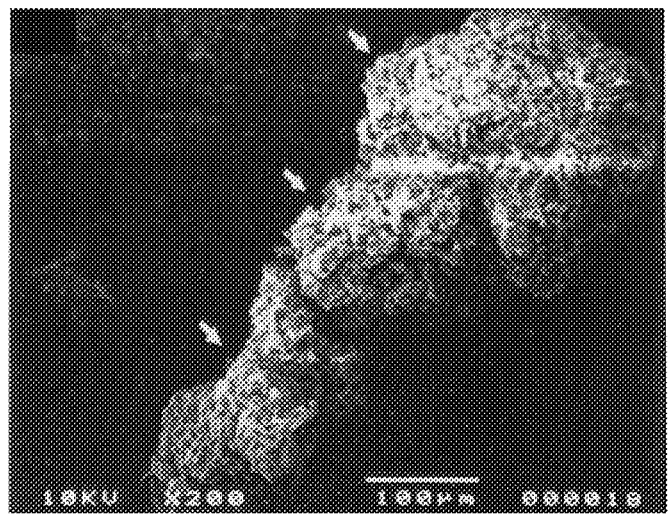
FIG. 1 is a view at 200× magnification of a three dimensional artificial normal organ tissue mass.

Aggregates of cells from the three major tissue groups were cultured in vitro. The artificially produced tissue masses exhibited normal morphology and cell function. Examples of organ tissue, structural tissue and blood tissue are described below.

The artificially produced mammalian organ tissue was generated from normal small intestine epithelial and mesenchymal cells. Human small intestine epithelial and mesenchymal cells were obtained from normal organs of patients, predominantly organ transplant donors, with no evidence of disease. The cells were then propagated in culture. The cells were initiated and propagated in M3 media supplemented with 2% fetal bovine serum (FBS), designated M3:2, for epithelial cells or with 10% FBS, designated M3:10, for mesenchymal cells. M3 medium is a complex base medium supplemented with many growth factors and nutrients including L-Broth (tryptone broth), bovine pituitary extract, hydrocortizone, essential and non-essential amino acids, pentagastrin, epidermal growth factor, transferrin, selenium, and insulin. Moyer, "Methods for Propagation and Characterization of Human GI and Other Cells for Study of HIV," J. Tiss. Cult. Meth., Vol. 13, pp. 107–116 (1991).

All cell cultures were grown in a Forma humidified $CO_2$ incubator with 95% air, 5% $CO_2$, and constant atmosphere at a temperature of 37° C. Normal mesenchymal cells were passaged as required by enzymatic dissociation with a solution of 0.1% Trypsin, 0.1% EDTA, for 15 minutes at 37° C. After incubation with the appropriate enzymes, the cells were centrifuged at 800×G for 10 minutes in Corning conical 15-ml centrifuge tubes. The cells were then resuspended in fresh medium and diluted into Corning T-flasks with 25 ml of fresh growth medium. Small intestine epithelial cells were passaged by dilution at a 1:2 ratio into fresh M3:2 medium in T-flasks. Cultures of epithelial cells were derived from the ileum and jejunum of three male donors (22–35 years of age). Mesenchymal cells were obtained from the submucosa of five donors (4 males, 17–27 years old, and a 2-month-old female).

Normal mesenchymal cells were removed from T-75 flasks by enzymatic digestion, washed once with calcium- and magnesium-free PBS (CMF-PBS), and assayed for viability by Trypan Blue dye exclusion (GIBCO). Cells were held on ice in fresh growth medium until inoculation. In the preferred process the primary inoculum introduced into the culture vessel was $2\times10^5$ mesenchymal cells/ml in a 125-ml volume with 5 mg/ml Cytodex-3 microcarrier beads (Pharmacia, Piscataway, N.J.). Cytodex-3 microcarriers were Type I, collage-coated dextran beads, 175 microns in diameter. After the primary inoculum was prepared for seeding, it was transferred to a culture vessel filled with culture media and cultured at microgravity conditions.

In a preferred method the microgravity conditions were simulated in unit gravity by a horizontal rotating wall vessel (RWV). A preferred RWV bioreactor is described in U.S. Pat. No. 5,026,650 to Schwarz et al. issued Jun. 25, 1991 and is incorporated by reference herein. The rotation of the culture vessel (bioreactor) was controlled to produce the simultaneous conditions of (1) collocation of cells and culture matrix with similar or differing sedimentation properties in a similar spatial region, (2) freedom for three dimensional spatial orientation of tissues formed by the culturing of the cells and (3) low shear and essentially no relative motion of the culture environment with respect to the walls of the culture vessel. The trajectory of the cell aggregates was determined. The speed of the rotation of the culture vessel was increased if the cell aggregates fell excessively inward and downward on the downward side of the rotational cycle and excessively outward and insufficiently upward on the upgoing side of the rotational cycle to prevent wall impact. The rotation of the culture vessel was decreased in response to excessive accumulation of tissue aggregation near the outer wall of the culture vessel so as not to restrict three dimensional growth. As the tissue aggregates grow the rotation was adjusted to obtain minimal collision frequency and intensity.

The culture media used in the RWV can be varied. A 1:1 mixture of M3:2 medium and standard minimal essential medium-alpha (MEM-alpha) .(GIBCO) supplemented with 10% FBS was used. A preferred media designated GTSF-2 was found to meet the growth requirements of the system without the need for unique growth factors and other complex components found in other media including M3:2. The GTSF-2 media is a trisugar-based medium with glucose, galactose and fructose supplemented with 6% FBS. A preferred formulation for GTSF-2 media is listed in Table 1 below. The pH was adjusted to 7.4 with 1N NaOH.

TABLE 1

| Tri-Sugar Based Medium GTSF-2 | | |
|---|---|---|
| Component | Concentration | Source/Order or Designation |
| MEM-alpha supplemented with 2.25 gm/L $NaHCO_3$ | 400 ml (40%) | GIBCO/430–1900EB |
| L-15 | 600 ml (60%) | GIBCO/430–1300EB |
| $NaHCO_3$ | 1.35 gm/liter | Sigma/S-5761 |
| HEPES | 3.0 gm/liter | Research Organics/6003H-2 |
| Folic acid | 6.667 µg/liter | Sigma/F-8758 |
| 0.5% Nicotinic acid | 0.667 ml/liter | Sigma/N-4126 |
| Bactopeptone | 0.6 gm/liter | Difco/0118-01 |
| I-inositol | 0.024 gm/liter | Sigma/I-5125 |
| Fructose | 0.13 gm/liter | Sigma/F-3510 |
| Galactose | 0.25 gm/liter | Sigma/G-5388 |
| D-Glucose | 1.0 gm/liter | Sigma/G-5250 |
| 300mM L-Glutamine | 10 ml/liter | Sigma/G-5763 |
| Gentamycin | 1 ml/liter | GIBCO/600–5750AD |
| Fungizone | 2 ml/liter | GIBCO/600–5295AE |
| Insulin-transferrin-sodium-solenite | 5 ml/liter | Sigma/I-1884 |
| Fetal bovine serum | 60 ml (6%) | Hyclone/A-1111-L |

The primary inoculum of mesenchymal cells was allowed to grow for a minimum of 2–3 days before the medium was changed. Then $2\times10^5$ epithelial cells/ml were added prepared as described above for the mesenchymal cells. The organ tissue can be bioengineered to develop desired patterns of cell layering by preselecting the introduction of the epithelial cells into the culture vessel. Also, the cells can be introduced essentially simultaneously into the vessel to produce normal organ tissue.

Culture conditions included mass transfer with exchange of nutrients for metabolic waste and appropriate gas exchange in the culture system. Fresh medium was replenished by 65% of the total vessel volume each 20 to 24 hours. As metabolic requirements increased, fresh medium was supplemented with an additional 100 mg/dl of glucose. Viable cocultures grown in the RWVs were harvested over periods up to 45 days and prepared for various assays.

The artificial organ tissue mass was produced in the RWV in both a 1:1 mixture of M3:2 and MEM alpha supplemented with 10% fetal bovine serum (Hyclone Laboratories, Logan, Utah) and tri-sugar based media shown in Table 1 on a preferred culture matrix of 5 mg/ml Cytodex-3 generally spherical microcarriers (Pharmacia, LKB). The three dimensional tissue cultures grown in the M3:2 and MEM media attained cell densities of $2.3-3.2 \times 10^5$ cells/ml and although the cultures did not reach plateau phase, suggesting the potential for continued growth, the epithelial cell contingent exhibited signs of considerable stress while the mesenchymal cells proliferated well.

The preferred tri-sugar based media was found to meet the growth requirements without the need for multiple growth factors and supplements. The cultures in the tri-sugar based media produced slightly higher average cell densities, 4.6 to $6.2 \times 10^6$ cells/ml as compared to the M3:2 and MEM media which exhibited cell densities of $2.5-3.2 \times 10^6$ cells/ml. The three dimensional tissue mass grown in the tri-sugar based media exhibited an epithelial cell component which appeared to proliferate in a more normal and appropriate fashion. The cultures were not grown to the plateau phase, indicating further capability for continued growth. The artificial tissue did not reach maximum cell densities after 38–45 days of culture.

The tissue masses grew to relatively large sizes as compared to other in vitro methods. After 300 hours of culture the tissue/microcarrier mass was about 0.2–0.3 cm in size with masses increasing to about 0.4–0.6 cm after approximately 500 hours of culture and over 0.6 cm after 800 hours of culture.

The epithelial cells and mesenchymal cells used to seed the cultures were immunophenotyped and compared to the three dimensional tissue cultured in the RWV. Samples were harvested at intervals during the culture process for immunocytochemical analysis. The antibodies used to immunochemically characterize the cell types are listed in Table 2 below.

TABLE 2

ANTIBODIES USED FOR IMMUNOCYTOCHEMICAL ANALYSIS

| Antibody Specificity | Dilution | Source/Order No. or Designation |
|---|---|---|
| Pancytokeratin | prediluted | DAKO, Inc./L1824 |
| Vimentin | prediluted | DAKO, Inc./L1843 |
| Factor VIII | prediluted | DAKO, Inc./L1809 |
| Villin | 1:20 | Chemicon, Temacria, CA/MAB 1671 |
| Sucrase | 1:20 | A. Elbein, UTHSCSA/YT |
| Angioblasts | 1:20 | Accurate Chem, Westbury CA/HE3-5/47 |
| Laminin | 1:20 | ICN, Costa Mesa, CA/69–630 |
| Fibronectin | 1:20 | US BIOCH, Cleveland, OH/33752 |
| Proteoglycan | 1:20 | Biological Products for Science, Oxford, UK/MCA 326 |
| Collagen Type IV | 1:20 | DAKO, Inc./M785 |

The keratin, vimentin, and Factor VIII antibodies detect epithelial, fibroblastic, and endothelial cells, respectively. Villin is a cytoskeletal protein only found in epithelial cells from small intestine and colon. The angioblast marker is present in subsets of precursor endothelial cells, particularly dividing cells. Sucrase is an enzyme found in the epithelial cell brush border of the small intestine. Basement membrane and extracellular matrix components laminin, fibronectin, Collagen IV, and proteoglycan were also assayed to determine their expression in the artificially produced three dimensional tissues.

Cultured organ tissue grown on Cytodex-3 microcarriers in the RWV were fixed in OmniFix, an alcohol-based fixative not containing aldehydes or mercury (Xenetics Biochemic, Tustin, Calif.). At all times, extreme care was taken not to damage the delicate artificial tissue comprised of cellular material and microcarrier beads. When an abundance of beads was present, the supernatant fluid was carefully decanted and a sample of beads was enclosed in a biopsy bag, then placed in a cassette to prepare a paraffin block. When bead clusters were scarce, a Shandon Cytoblock Kit (Shandon Inc., Pittsburgh, Pa.) was used. Cassettes were processed in a standard tissue processor. Five-micron sections were cut from the paraffin-embedded tissues, deparaffinized by standard procedures, then assayed by incubation with the test antibodies (Table 2) followed by use of the universal labeling streptavidin biotin (LSAB) kit (DAKO Inc., Carpenteria, Calif., No. K680), which detects mouse monoclonal and rabbit polyclonal antibodies. The immunocytophenotyping was confirmed by one positive and two negative controls. The positive control was normal tissue-sections or normal cells positive for the primary antibody used. The negative controls were 1) PBS only, to test for false binding by "link" antibody and streptavidin, and 2) normal serum of the same species from which the primary antibody was prepared.

Analysis by immunocytochemistry was used to confirm the ability of the seed cells to produce a three dimensional artificially produced tissue mass with functional epithelial cells and functional mesenchymal cells as well as functional precursor endothelial cells that were not present in the seed culture. As the culture progressed and the tissue mass grew it included functional angioblasts.

Immunophenotyping of the cell types used to seed the coculture in the RWV confirmed the majority of epithelial and mesenchymal cells seeded were keratin and vimentin positive, respectively. In addition, the epithelial cells were at various stages of differentiation. Only a small percentage (<2%) of the cells was positive for Factor VIII, an endothelial cell differentiation marker. Table 3 is a summary of the immunochemical staining reaction of the three dimensional tissue of the present invention. The tissue was harvested at various intervals up to 41 days as noted in Table 3.

An increased percentage >10% of cells present in the masses consisted of endothelial cells which were Factor VIII positive as confirmed by immunochemistry and growing as patches on the beads. Furthermore, a small percentage, 1–2% of cells, showed de novo expression of the HE3 angioblast antigen which was not present in the seed cultures of mesenchymal cells confirming the presence of angioblasts in the tissue by immunochemistry. Functional cell brush borders were confirmed immunochemically by the presence of sucrase.

Figure 2:
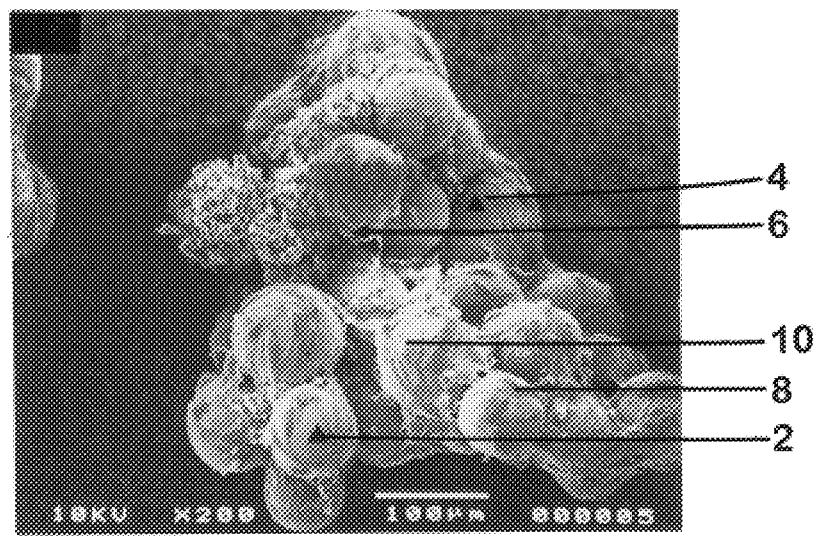
FIG. 2 is a photograph of artificial normal organ tissue at 200× magnification.
Figure 3:
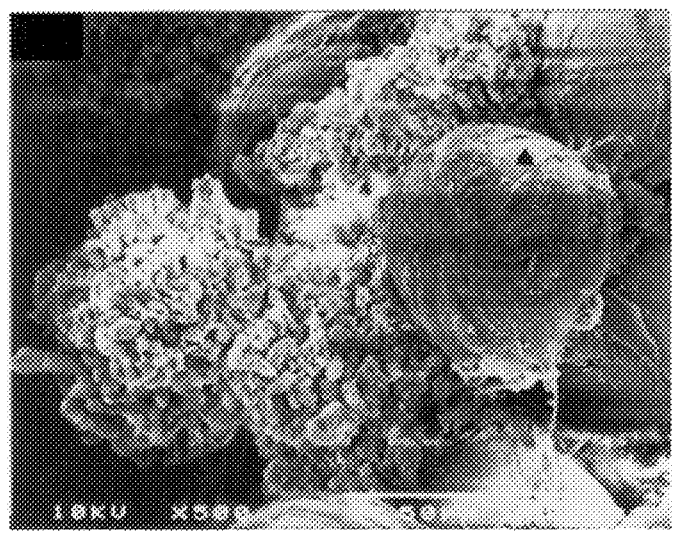
FIG. 3 is a photograph of artificial normal organ tissue at 500× magnification.
Figure 4:
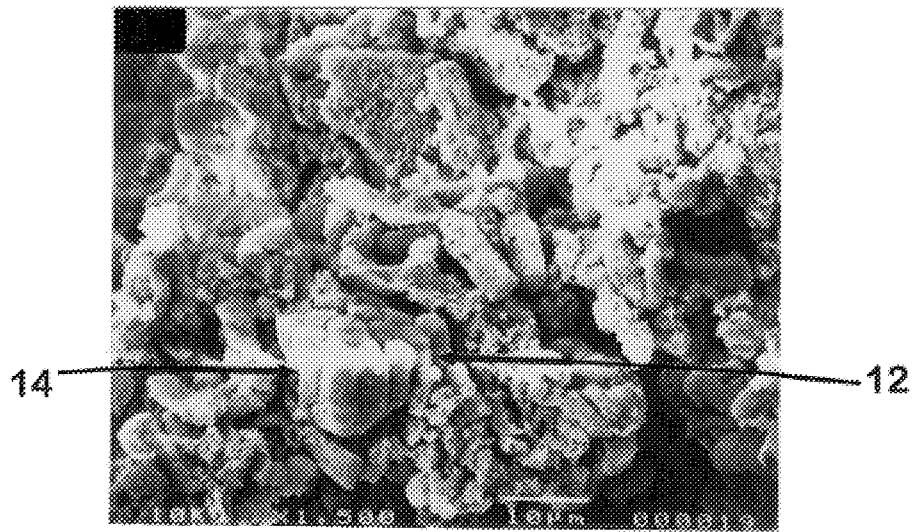
FIG. 4 is a photograph of artificial normal organ tissue at 1500× magnification.
Figure 5:
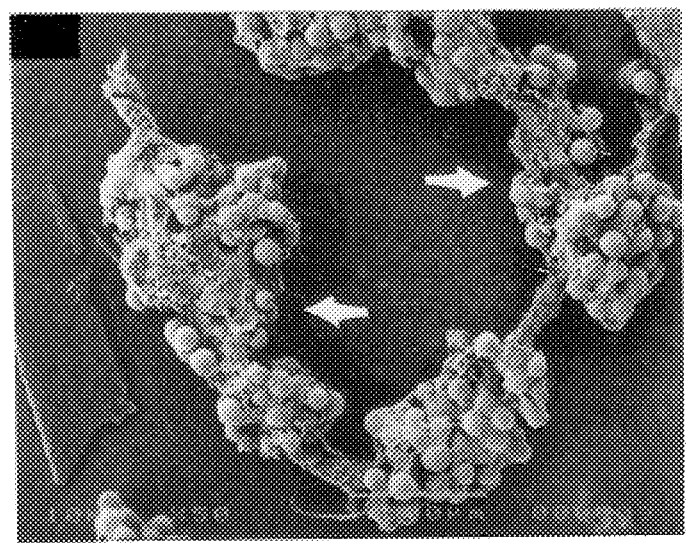
FIG. 5 is a photograph of artificial normal organ tissue at 50× magnification.

FIG. 1 is a photograph of the small intestine artificially produced organ tissue at 200× magnification showing the three dimensional cell aggregate generally indicated by the arrows. FIG. 2 is a photograph of the small intestine organ tissue. The triangular markers at 2 and 4 in the photograph are for reference on the microcarriers. A mass of epithelial cells is shown at 6. Elongated mesenchymal cells are growing on the microcarriers as shown at 8 and 10. FIG. 3 is a higher magnification (500×) of the epithelial mass shown at 6 in FIG. 2. FIG. 4 shows the organized columnar epithelial cells of the small intestine organ tissue at arrows 12 and 14. FIG. 5 shows the three dimensional organ tissue masses joined by cord-like structures of fibroblasts (mesenchymal cells) covered by epithelial cells.

TABLE 3

SUMMARY OF IMMUNOCHEMICAL STAINING ON TISSUE GROWTH IN RWV*

| Antibodies | Specificity or Cell Stained | Days Grown in RWV | | | | |
|---|---|---|---|---|---|---|
| | | 13 | 23 | 25 | 37 | 41 |
| Keratin | Epithelial, Cytoskeletal | +++ | +++ | ++ | ++ | ++ |
| Vimentin | Fibroblasts, some endothelial | +++ | +++ | ++ | ++ | ++ |
| Factor VIII | Endothelial | ++ | +++ | ++ | ++ | ++ |
| Villin | Epithelial, small intestine | + | + | + | + | + |
| HE3 | Angioblasts | − | − | − | ++ | ++ |
| Sucrase | Small intestine, cell brush border | +++ | + | ++ | ++ | ++ |
| Laminin | Basement membrane | + | + | − | + | ++ |
| Fibronectin | Basement membrane | + | + | ++ | ++ | — |
| Proteoglycan | Extracellular matrix | ++++ | ++++ | ++++ | ++++ | ++++ |
| Collagen Type IV | Extracellular matrix | ++ | + | + | ++ | ND |

*Slides were observed and scored on a relative scale as − (negative) to ++++ (maximum staining; very dark positive for >90% of the cells); + indicates weaker staining for ~25–50% of the cells; ++ indicates moderate staining for greater than 50–75% of the cells.

Samples from the RWV cultures were taken for scanning electron microscopy at the same times as those taken for immunocytochemistry. After removal from the reactor vessels, samples were washed once with CMF-PBS. The samples were suspended in a buffer containing 3% glutaraldehyde and 2% paraformaldehyde in 0.1M cacodylate buffer at pH 7.4, then rinsed for 5 minutes with cacodylate buffer three times and postfixed with 1% osmium tetroxide (Electron Microscopy Sciences, Fort Washington, Pa.) in cacodylate buffer for 1 hour. Samples were then rinsed for 5 minutes with distilled water three times and then treated for 10 minutes with Millipore (Millipore Corp., Bedford, Mass.) (0.2$\mu$) filtered, saturated solution of thiocarbohydrazide (Electron Microscopy Sciences), then washed for 5 minutes with distilled water five times and fixed with 1% buffered osmium tetroxide for 10 minutes. This last step was necessary to prevent the microcarriers from collapsing. Samples were then rinsed with distilled water three times and dehydrated with increasing concentrations of EtOH followed by three changes in absolute methanol. After transfer to 1, 1, 1, 3, 3, 3-hexamethyldisilazane (HMDS) (Electron Microscopy Sciences) samples were allowed to soak for 10 minutes, drained, and air dried overnight. Dried samples were sprinkled with a thin layer of silver paint on a specimen stub, dried, coated by vacuum evaporation with platinum-palladium alloy, and then examined in the JEOL T330 Scanning electron microscope at an accelerating voltage of 5 to 10 kV.

Micrographs taken of 6- to 7-day cocultures showed partial coverage of the microcarriers by normal small intestine mesenchymal cells. Additionally, large developing masses of small intestine epithelium were evident, growing on the microcarrier beadpacks. Samples harvested at approximately 12 days of culture contained small microcarrier packs which were totally engulfed in proliferating small intestine epithelium. Micrographs of samples at 13 days displayed large tissue-like masses that were entirely covered with small intestine epithelium grown on a base layer of mesenchymal cells. Areas of organized columnar epithelium were prominent. As the cultures matured into mid- and late-stage cultures, extremely complex tissue-like masses comprised of mesenchymal and epithelial cells were seen from approximately 16 days of culture until termination at 41 days. These tissues were assembled from smaller masses which were joined by cord-like structures of fibroblasts and covered by epithelial cells several layers deep. In addition, available microcarriers were drawn to the surface of these large masses which were approximately 0.3 to 0.5 cm in diameter. Finally, columnar epithelium was observed to be growing even in the recessed areas of the microcarrier bead packs.

The artificially produced mammalian structural tissue was generated from normal mouse embryonic femurs. The fetal cells are a mixture of chondrocytes and stromal cells. The cells were placed in a standard media commonly designated as CMRL 1066 (Gibco Labs) containing 10% Fetal Bovine Serum. The cells were disassociated by standard enzymatic digestion. The single cells produced by enzymatic digestion were washed several times in PBS and transferred into a culture vessel with fluid culture media. The preferred culture vessel is described in U.S. Pat. No. 5,026,650 and referenced above. The vessel was steam sterilized by autoclaving at standard temperature and pressure prior to transfer of the cells.

A preferred culture matrix of generally spherical microcarrier Cytodex-3 beads were transferred into the culture vessel. The approximate total cell inoculum was 132,000,000 at a ratio of 30 cells per Cytodex-3 microcarrier bead. The bead concentration of the vessel was 10 mg/ml (4000 beads/mg). The culture media in the vessel was CMRL 1066 with ascorbic acid 10 mg/ml added.

Microgravity conditions were simulated in culture vessel as described and referenced herein. The vessel provided the quiescent well-perfused environment for maintenance of cell surface receptors and undisturbed cell-to-cell co-location. Co-location is important for autocrine-paracrine factor formation and exchange between cellular types, and nurturing of differentiation with consequential matrix deposition. The cells were cultured for up to 65 days. The tissue masses grew to at least 0.4 cm in length after 1000 hours of culture. The development of normal cartilage tissue was evidenced by normal morphology of the chondrocyte and stromal cell formation and cartilagineous tissue substructures. Also, tissue with calcification was produced. Also, proteoglycan deposition was identified. The normal pattern of Type II collagen deposition followed by down regulation of Type II collagen deposition and enhanced formation of Type IX and Type X collagen was observed.

Figure 6:
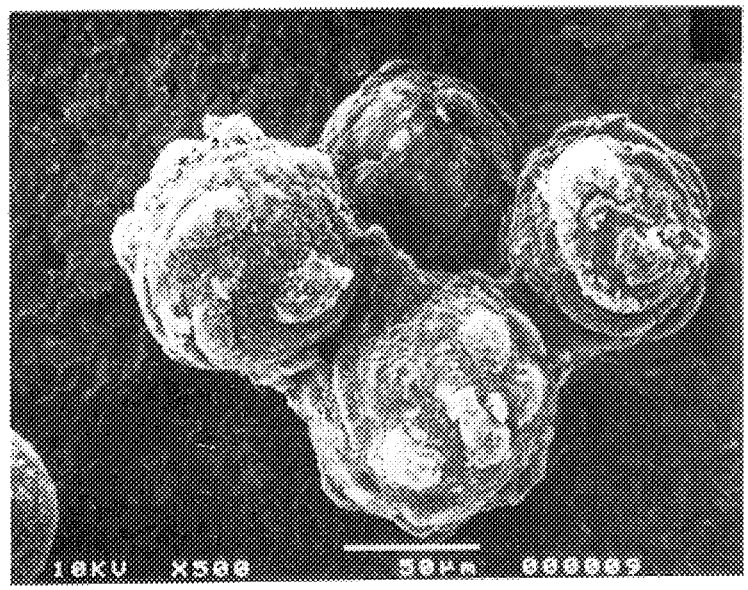
FIG. 6 is a photograph of artificial normal structured tissue at 500× magnification.
Figure 7:
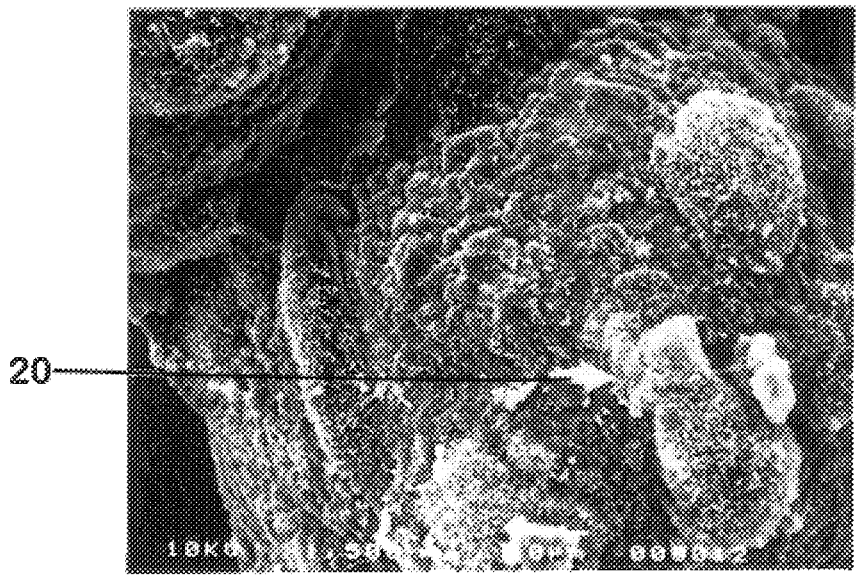
FIG. 7 is a photograph of artificial normal structural tissue at 1500× magnification.
Figure 8:
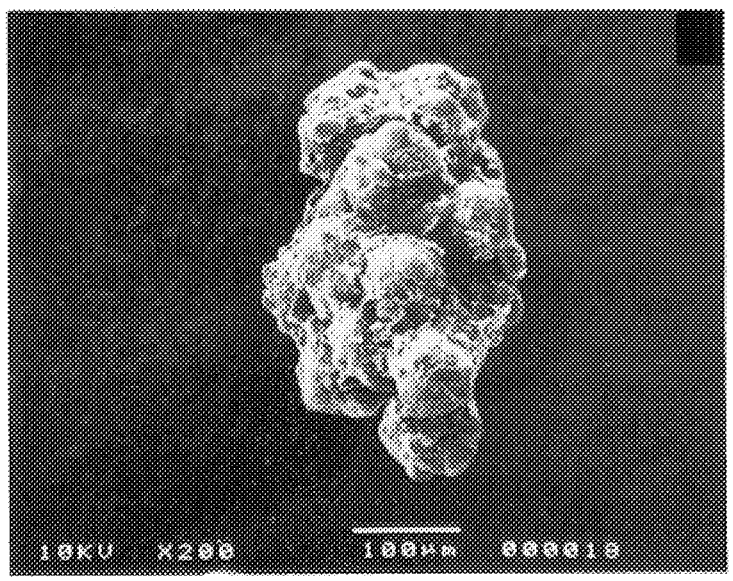
FIG. 8 is a photograph of artificial normal structural tissue at 200× magnification.
Figure 9:
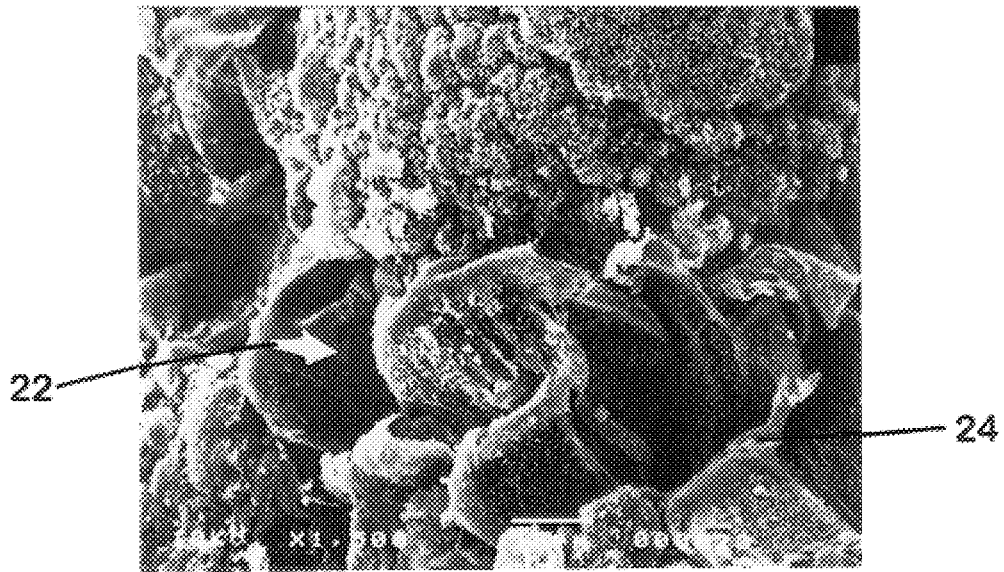
FIG. 9 is a photograph of artificial normal structural tissue at 1500× magnification.

Photographs taken during the culture period of the structural cells show the growth and normal development of the tissue. FIG. 6 is a micrograph taken at 500× magnification at 300 to 600 hours of culture of normal fetal mouse chondrocytes. The cells grew around the generally spherical microcarriers. FIG. 7 is a higher magnification showing preliminary calcification at the arrow 20. FIGS. 8 and 9 were taken after 900 to 1100 hours of culture with differentiated fibroblastic chondrocytes shown in FIG. 9 at 22. Also, stromal cells are show in FIG. 9 at 24.

The artificially produced blood tissue can be made from human bone marrow samples or other sources of mammalian origin. Human bone marrow samples are obtained by standard clinical techniques under aseptic conditions. In general, a bone marrow tool is used to puncture the bone and obtain a bone marrow sample that is fully inclusive of normal constituents. The normal constituents will include, but are not limited to: pleuripotential stem cells, fully maturated white blood cells and red blood cells, stromal components, and cells in intermediate stages of maturation.

Laboratory animals such as mice can be used as a source of bone marrow for selected studies. After sacrificing mice, the femur and tibia are removed and placed in 1×Calcium- and Magnesium-free PBS with 200 μg/ml pen-strep. Muscle is removed and endcaps of the bones are cut. With a syringe and 26G needle, the bone is flushed with cold complete growth medium known to those skilled in the art such as CMRL 1066. Cells are then poured through collector screens to remove large pieces of tissue and suspended cells are placed in 50-cc sterile tubes on cold complete growth medium. Cells are washed and centrifuged three times to insure no contamination. Cells are not treated with any reagent to remove red blood cells.

The preferred culture vessel is described in U.S. Pat. No. 5,026,650 previously cited and incorporated by reference herein. A fluid culture media is introduced into the sterilized vessel. A preferred fluid culture media is a standard tissue culture media commonly designated as RPM1-1640 (available from Gibco and other sources).

The sterile bone marrow cells are then transferred to fluid culture medium and suspended. Suspended cells are transferred, at approximate densities of $1 \times 10^6$ cells/ml, to the culture vessel. Various cell matrices can be used. The collected bone marrow cells can be encased in stromal-like matrices. The matrices can be disc-shaped. Other matrices are generally known can be used including, but are not limited to, collagen matrices of Type I rat tail collagen or other biopolymeric matrices. The biopolybers used can be biodegradable such as suture materials. Cross-linked polymers such as collagen, fibronectin and mixtures thereof may be used. These matrices may have spherical diameters ranging from 1 millimeter to 10 millimeters and include the necessary cellular constituents to facilitate primary bone marrow culture. Cytodex-3 microcarriers can be introduced into the vessel at a density of 5 mg/ml. Bone marrow cells contained in the matrix or supported in suspension are cultured at microgravity conditions and mass transfer as described herein and the incorporated references.

Early in the initiation it is preferable that the cells are allowed to grow and metabolize without sampling interruption. The first sampling may begin one to seven days after inoculation. Consequently, cellular aggregates are not disturbed and bone marrow growth factors are not diluted by media repletion. After the lag phase, media repletion is based upon requirements as previously described. Cellular phenotyping is carried out by flow cytometry and light microscopy.

Figure 10:
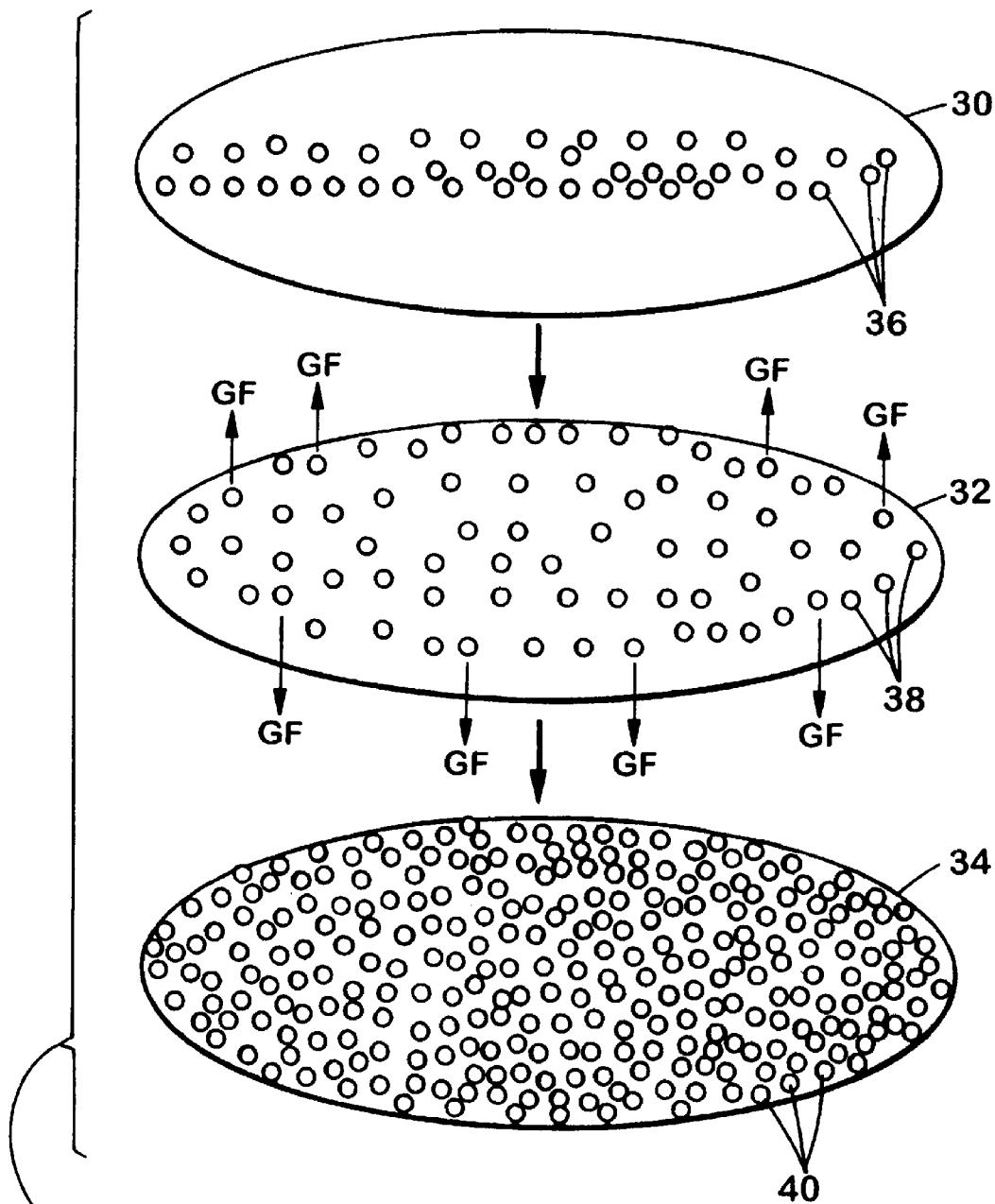
FIG. 10 is a schematic drawing of the blood producing tissue cells and microcarriers.

FIG. 10 is a schematic drawing of the bone marrow cell production. The disc-shaped culture matrices are shown at 30, 32 and 34. The bone marrow cells are shown as circular figures at 36, 38 and 40. The arrows with the GF generally indicate the excretion of growth factors from the normal bone marrow cells that enhance tissue growth in the culture system.

In the case of preparing bone marrow for recipients, volumes are expanded as cellular densities or metabolic requirements dictate. The limited parameters may depend upon the rotating vessel's ability to suspend large aggregates, in which case if unable to suspend large aggregates, smaller aggregates would be distributed through several vessels. If the metabolic requirements were such that mass transfer of oxygen and removal of carbon dioxide were not sufficient to maintain cellular growth and expansion, then cells would be aliquoted into additional vessels.

The examples included are not intended to limit the scope of the present invention. Normal mammalian cells have been cultured to produce aggregates of cells of three dimensional tissue masses. Other substitutions, modifications and variations are apparent to those skilled in the art without departing from the disclosure and scope of the invention.

What we claim is:

1. A culture medium for non-neoplastic mammalian organ tissue culture comprising:

(a) minimal essential medium-alpha (MEM-ALPHA™);
   (b) Leibovitz L-15™ medium;
   (c) tri-sugar supplement; and
   (d) serum.

2. The culture medium of claim 1 wherein the tri-sugar supplement is selected from mixtures of the group consisting of fructose, galactose, and glucose.

3. The culture medium of claim 2 wherein said concentration of fructose ranges from about 65 mg/liter to about 500 mg/liter.

4. The culture medium of claim 2 wherein said concentration of galactose ranges from about 125 mg/liter to about 900 mg/liter.

5. The culture medium of claim 2 wherein said concentration of glucose ranges from about 500 mg/liter to about 4500 mg/liter.

6. The culture medium of claim 1 wherein the medium further comprises sodium bicarbonate ($NaHCO_3$).

7. The culture medium of claim 1 wherein the MEM-ALPHA™ base medium and LEIBOVITZ L-15™ medium are in a 4:6 ratio.

8. The culture medium of claim 1 wherein said serum is selected from the group consisting of bovine serum and calf serum.

9. The culture medium of claim 1 wherein said serum concentration ranges from about 3% to about 25%.

10. The culture medium claim 1 further comprising gentamycin, fungizone, $NaHCO_3$, HEPES, folic acid, nicotinic acid, bactopeptone, i-inositol, L-glutamine, and insulin-transferrin-sodium selenite solution.

* * * * *